United States Patent
Grover et al.

(10) Patent No.: US 10,321,964 B2
(45) Date of Patent: Jun. 18, 2019

(54) ROBOTICALLY CONTROLLING SURGICAL ASSEMBLIES

(71) Applicant: Covidien LP, Mansfield, MA (US)

(72) Inventors: Simon R. Grover, Cambridge (GB); Charles F. Kilby, Cambridgeshire (GB); Daniel L. Fuller, Haverhill (GB); Alistair Ward, Swavesey (GB)

(73) Assignee: Covidien LP, Mansfield, MA (US)

( * ) Notice: Subject to any disclaimer, the term of this patent is extended or adjusted under 35 U.S.C. 154(b) by 22 days.

(21) Appl. No.: 15/510,799

(22) PCT Filed: Jul. 23, 2015

(86) PCT No.: PCT/US2015/041684
§ 371 (c)(1),
(2) Date: Mar. 13, 2017

(87) PCT Pub. No.: WO2016/043845
PCT Pub. Date: Mar. 24, 2016

(65) Prior Publication Data
US 2017/0273749 A1 Sep. 28, 2017

Related U.S. Application Data

(60) Provisional application No. 62/050,443, filed on Sep. 15, 2014.

(51) Int. Cl.
*A61B 34/35* (2016.01)
*A61B 34/30* (2016.01)
(Continued)

(52) U.S. Cl.
CPC ............ *A61B 34/35* (2016.02); *A61B 17/068* (2013.01); *A61B 34/30* (2016.02); *A61B 34/71* (2016.02);
(Continued)

(58) Field of Classification Search
CPC ......... A61B 34/35; A61B 34/71; A61B 34/70; A61B 34/76; A61B 2034/304; A61B 17/068
(Continued)

(56) References Cited

U.S. PATENT DOCUMENTS 6,246,200 B1 * 6/2001 Blumenkranz ........ B25J 9/1689
128/DIG. 7
6,461,372 B1 10/2002 Jensen et al.
(Continued)

FOREIGN PATENT DOCUMENTS

EP 1815949 8/2007
EP 1815949 A1 8/2007
(Continued)

OTHER PUBLICATIONS

International Search Report for (PCT/US2015/041684) date of completion is Oct. 22, 2015 (4 pages).
(Continued)

*Primary Examiner* — Pedro Philogene
*Assistant Examiner* — David C Comstock

(57) ABSTRACT

A surgical system for selective connection to a robotic arm includes an instrument drive unit, an instrument support platform coupled to the instrument drive unit, an instrument carriage coupled to the instrument support platform, and a surgical instrument releasably coupled to the instrument carriage. The surgical instrument includes an end effector controllable to perform surgery in response to telemanipulation of actuators in the instrument drive unit.

21 Claims, 9 Drawing Sheets

(51) Int. Cl.
*A61B 34/00* (2016.01)
*A61B 17/068* (2006.01)
*A61B 17/00* (2006.01)

(52) U.S. Cl.
CPC .............. *A61B 34/70* (2016.02); *A61B 34/76* (2016.02); *A61B 2017/00477* (2013.01); *A61B 2034/302* (2016.02); *A61B 2034/304* (2016.02)

(58) Field of Classification Search
USPC ..... 606/1, 130; 128/903, 904; 600/204, 228, 600/229
See application file for complete search history.

(56) References Cited

U.S. PATENT DOCUMENTS

| | | | |
|---|---|---|---|
| 7,204,844 B2 | 4/2007 | Jensen et al. | |
| 7,331,967 B2 | 2/2008 | Lee et al. | |
| 7,594,912 B2 * | 9/2009 | Cooper | A61B 19/2203 600/102 |
| 8,241,271 B2 | 8/2012 | Millman et al. | |
| 8,491,603 B2 | 7/2013 | Yeung et al. | |
| 8,506,555 B2 | 8/2013 | Ruiz Morales | |
| 8,602,031 B2 | 12/2013 | Reis et al. | |
| 8,708,952 B2 | 4/2014 | Cohen et al. | |
| 8,720,448 B2 | 5/2014 | Reis et al. | |
| 8,777,934 B1 | 7/2014 | Tan et al. | |
| 8,828,023 B2 | 9/2014 | Neff et al. | |
| 2004/0049205 A1 | 3/2004 | Lee et al. | |
| 2006/0084945 A1 | 4/2006 | Moll et al. | |
| 2007/0233052 A1 | 10/2007 | Brock | |
| 2010/0204646 A1 | 8/2010 | Plicchi et al. | |
| 2010/0204713 A1 | 8/2010 | Ruiz Morales | |
| 2011/0015650 A1 | 1/2011 | Choi et al. | |
| 2011/0118754 A1 | 5/2011 | Dachs, II et al. | |
| 2011/0245844 A1 | 10/2011 | Jinno | |
| 2011/0277775 A1 | 11/2011 | Holop et al. | |
| 2012/0071752 A1 * | 3/2012 | Sewell | A61B 6/12 600/424 |
| 2012/0165828 A1 | 6/2012 | Duque et al. | |
| 2012/0209291 A1 | 8/2012 | Anderson et al. | |
| 2012/0277764 A1 | 11/2012 | Cooper et al. | |
| 2013/0123783 A1 | 5/2013 | Marczyk et al. | |
| 2013/0172713 A1 | 7/2013 | Kirschenman | |
| 2013/0282021 A1 | 10/2013 | Parihar | |
| 2013/0317519 A1 | 11/2013 | Ramo et al. | |
| 2013/0325034 A1 | 12/2013 | Schena et al. | |
| 2014/0046340 A1 | 2/2014 | Wilson et al. | |
| 2014/0276761 A1 | 9/2014 | Parihar et al. | |
| 2015/0297199 A1 | 10/2015 | Nicholas et al. | |

FOREIGN PATENT DOCUMENTS

| | | |
|---|---|---|
| WO | 2009120944 A2 | 10/2009 |
| WO | 2011-060318 A1 | 5/2011 |
| WO | 2014-163787 A1 | 10/2014 |

OTHER PUBLICATIONS

European Search Report issued in European Application No. EP 15841989.5-1115 dated Apr. 30, 2018.
International Search Report and Written Opinion issued in PCT/US2016/014213 dated May 13, 2016.
International Search Report and Written Opinion issued in PCT/US2016/031594 dated Aug. 18, 2016.
International Search Report and Written Opinion issued in PCT/US2016/034509 dated Sep. 12, 2016.
Chinese Office Action (with English translation) dated Nov. 23, 2018 in corresponding Chinese Application No. 201580049152.3, 18 pages.

* cited by examiner

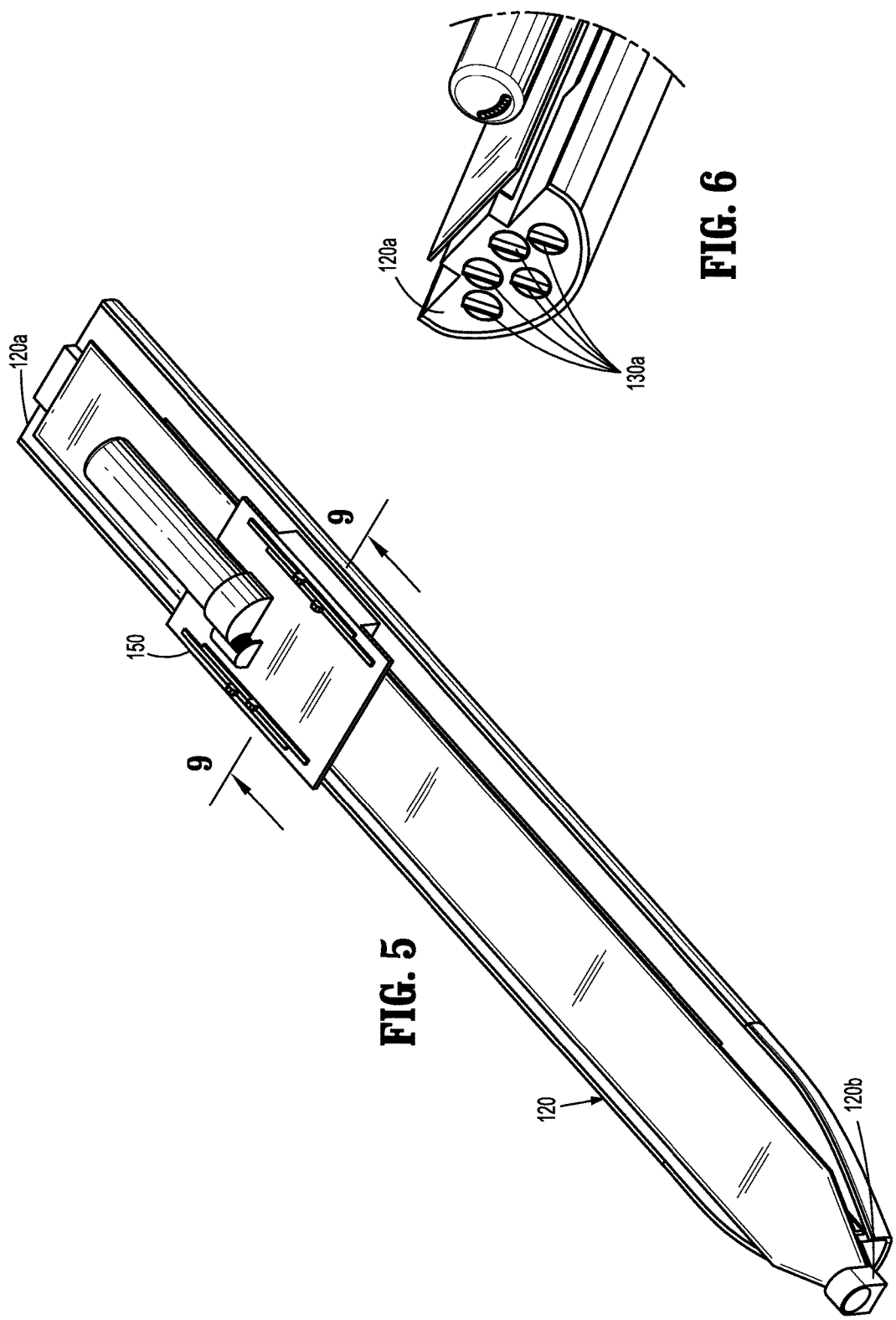

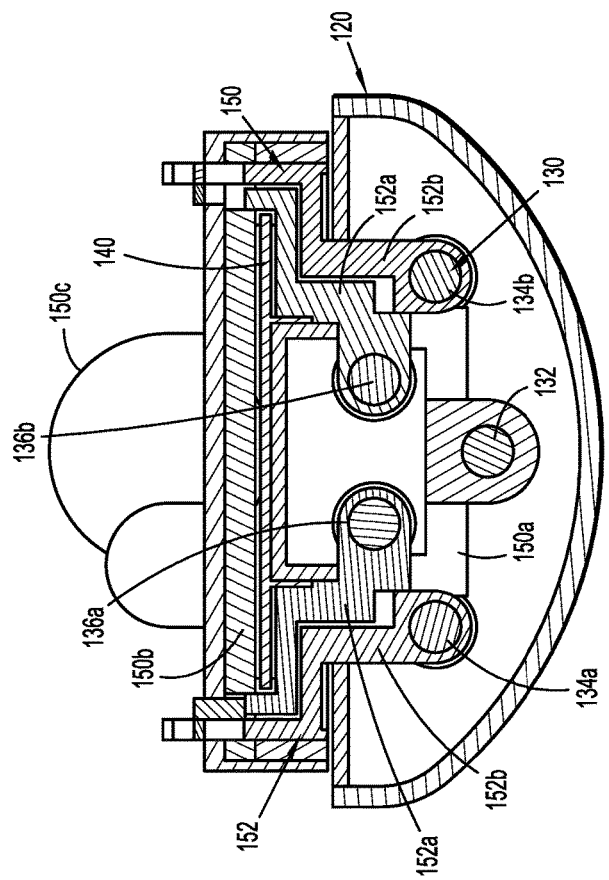
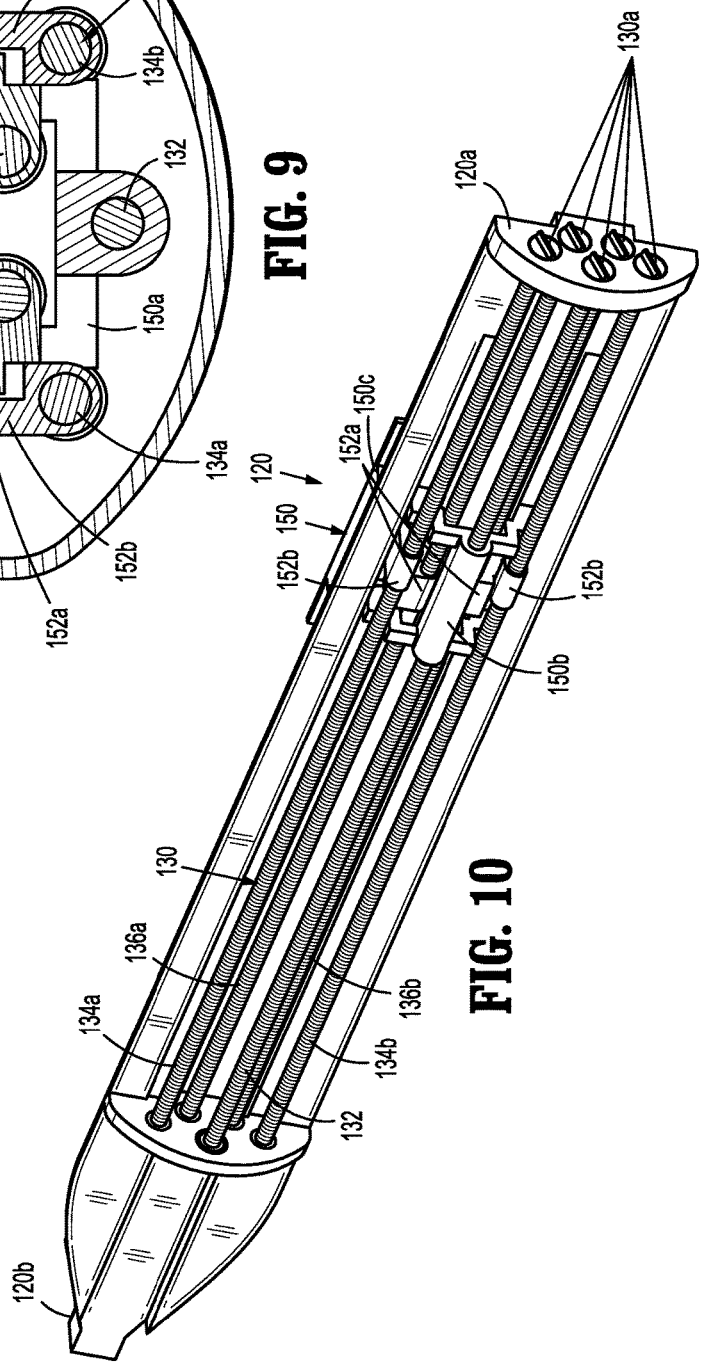
FIG. 9
FIG. 10

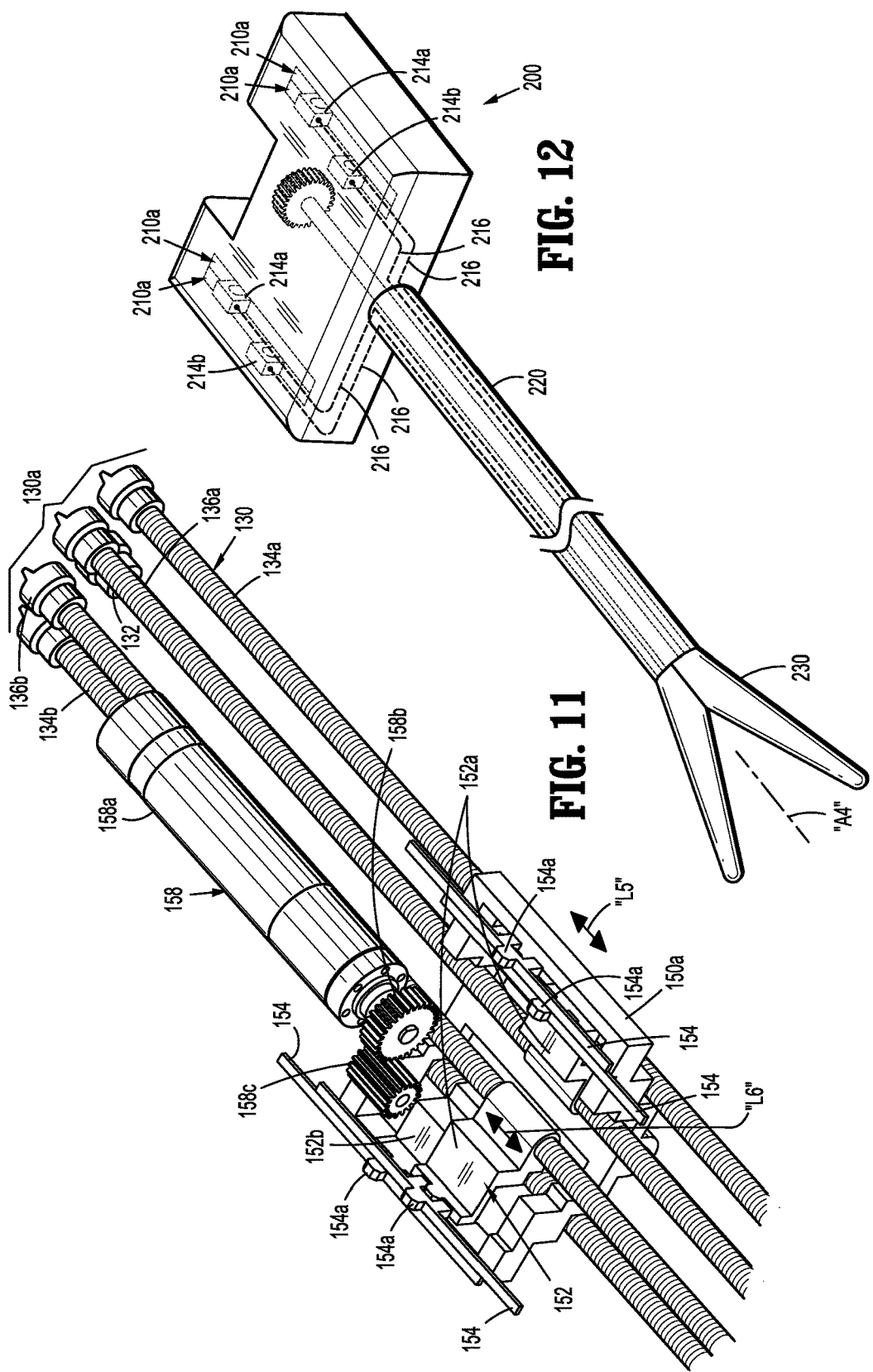

ROBOTICALLY CONTROLLING SURGICAL ASSEMBLIES

CROSS-REFERENCE TO RELATED APPLICATIONS

This application is a U.S. National Stage Application filed under 35 U.S.C. § 371(a) of International Patent Application No. PCT/US2015/041684, filed Jul. 23, 2015, which claims the benefit of and priority to U.S. Provisional Patent Application No. 62/050,443, filed Sep. 15, 2014, the entire disclosure of which is incorporated by reference herein.

TECHNICAL FIELD

The present disclosure relates to robotics, and more specifically to robotic surgical devices, assemblies, and/or systems for performing endoscopic surgical procedures and methods of use thereof.

BACKGROUND

Robotic surgical systems used in minimally invasive medical procedures include a console supporting a robot arm and a surgical instrument having an end effector that may include, for example, forceps, a stapler, or a grasping tool. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult. Further, cables for actuating functions of the surgical instrument can become entangled upon rotation of the surgical instrument relative to the instrument drive unit.

SUMMARY

Accordingly, new robotic devices, systems, and methods that are reliable, precise, and that enable easy and efficient attachment and removal of surgical instruments thereto would be desirable.

The present disclosure describes robotic devices, systems, and methods that demonstrate a practical approach to meeting the performance requirements and respect the usability challenges associated with instrument attachment and removal. In general, the present disclosure describes robotic surgical systems that include an instrument drive unit, an instrument support platform coupled to the instrument drive unit, an instrument carriage coupled to the instrument support platform, and a surgical instrument releasably coupled to the instrument carriage. The surgical instrument includes an end effector controllable to perform surgery in response to telemanipulation of actuators in the instrument drive unit.

In accordance with an aspect of the present disclosure, a surgical system for selective connection to a robotic arm is provided. The surgical system includes an instrument drive unit including actuators, an instrument support platform releasably coupled to the instrument drive unit, an instrument carriage coupled to rotatable members of the instrument support platform, and a surgical instrument releasably coupled to the instrument carriage. The actuators of the instrument drive unit may be controlled by telemanipulation.

In embodiments, the instrument drive unit includes a gear actuatable by one of the actuators. The instrument support platform and the surgical instrument may be simultaneously rotatable about a longitudinal axis defined through the instrument support platform in response to actuation of the gear.

The instrument support platform includes rotatable members operably associated with the actuators of the instrument drive unit. Each of the rotatable members is rotatable in response to actuation of one or more of the actuators.

The instrument carriage includes drive members that are translatable in response to rotation of one or more of the rotatable members. In embodiments, rotation of one or more of the rotatable members linearly translates a carriage body of the instrument carriage through one or more channels defined by the instrument support platform to move the instrument carriage relative to the instrument support platform. A barrier may cover the one or more of the channels. In some embodiments, a plurality of spaced apart channels extends longitudinally along the instrument support platform.

In some embodiments, one or more of the drive members rotates a first driven member of the surgical instrument and one or more of the drive members linearly translates a second driven member of the surgical instrument. In response to movement of a respective one of the first and second driven members, the respective one of the first and second driven members is configured to effectuate movement of the end effector relative to the instrument support platform and/or a firing of the end effector. One or more of the drive members may include a drive gear that is configured to engage a driven gear of the first driven member. In some embodiments, one or both of the first and second driven members includes a cable that operatively couples to the end effector. In embodiments, one or both of the first and second driven members includes a rod that operatively couples to the end effector.

The surgical instrument supports an end effector that extends distally from the instrument support platform. The end effector is movable in response to translation of one or more of the drive members of the instrument carriage.

According to one aspect, a robotic surgical assembly includes a robotic arm including an arm mount. The robotic surgical assembly further includes an instrument drive unit secured to the arm mount and a plurality of actuators. An instrument support platform of the robotic surgical assembly defines a longitudinal axis and is releasably coupled to the instrument drive unit. The robotic surgical assembly further includes an instrument carriage coupled to the rotatable members.

The instrument carriage includes one or more rotary drive members that rotate about the longitudinal axis of the instrument support platform and one or more linear drive members that linearly translate along the longitudinal axis of the instrument support platform. One or more of the linear and rotary drive members is movable in response to rotation of one or more of the rotatable members of the instrument support platform.

In embodiments, the instrument drive unit and the arm mount include gears that engage one another to enable an end face of the instrument drive unit to rotate about a longitudinal axis defined through the instrument drive unit. The instrument support platform is connectable to the end face of the instrument drive unit so that that rotation of the end face imparts rotational movement on the instrument support platform.

According to another aspect, a surgical assembly for supporting a surgical instrument having an end effector is provided. The surgical assembly includes an instrument drive unit, an instrument support platform, and an instrument carriage.

The instrument support platform defines a longitudinal axis and is configured to releasably couple to the instrument drive unit. The instrument support platform includes a plurality of rotatable members.

The instrument carriage is coupled to the rotatable members and includes at a rotary drive member that rotates about the longitudinal axis of the instrument support platform and linear drive members that linearly translate along the longitudinal axis of the instrument support platform. The rotary drive member is configured to fire the end effector in response to a rotational movement of a first one of the rotatable members of the instrument support platform. One or more of the linear drive members is configured to move the end effector relative to the support platform in response to rotation of a second one of the rotatable members of the instrument support platform.

In embodiments, a third one of the plurality of rotatable members of the instrument support platform linearly translates a carriage body of the instrument carriage through one or more channels defined by the instrument support platform to move the instrument carriage relative to the instrument support platform.

In some embodiments, at least a first one of the plurality of rotatable members rotates independent of a second one of the plurality of rotatable members.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 5 is an enlarged perspective view of an instrument support platform of the surgical assembly shown in FIGS. 2 and 3;

FIG. 6 is an enlarged perspective view of the indicated area of detail illustrated in FIG. 3;

FIG. 9 is an enlarged cross-sectional view of the instrument support platform shown in FIG. 5 as taken along line segment 9-9;

FIG. 10 is an enlarged bottom perspective view of the instrument support platform shown in FIG. 5;

FIG. 11 is an enlarged perspective view of a portion of the instrument support platform shown in FIG. 5;

FIG. 12 is an enlarged perspective view of a portion of a surgical instrument of the surgical assembly shown in FIGS. 2 and 3;

DETAILED DESCRIPTION

Figure 1:
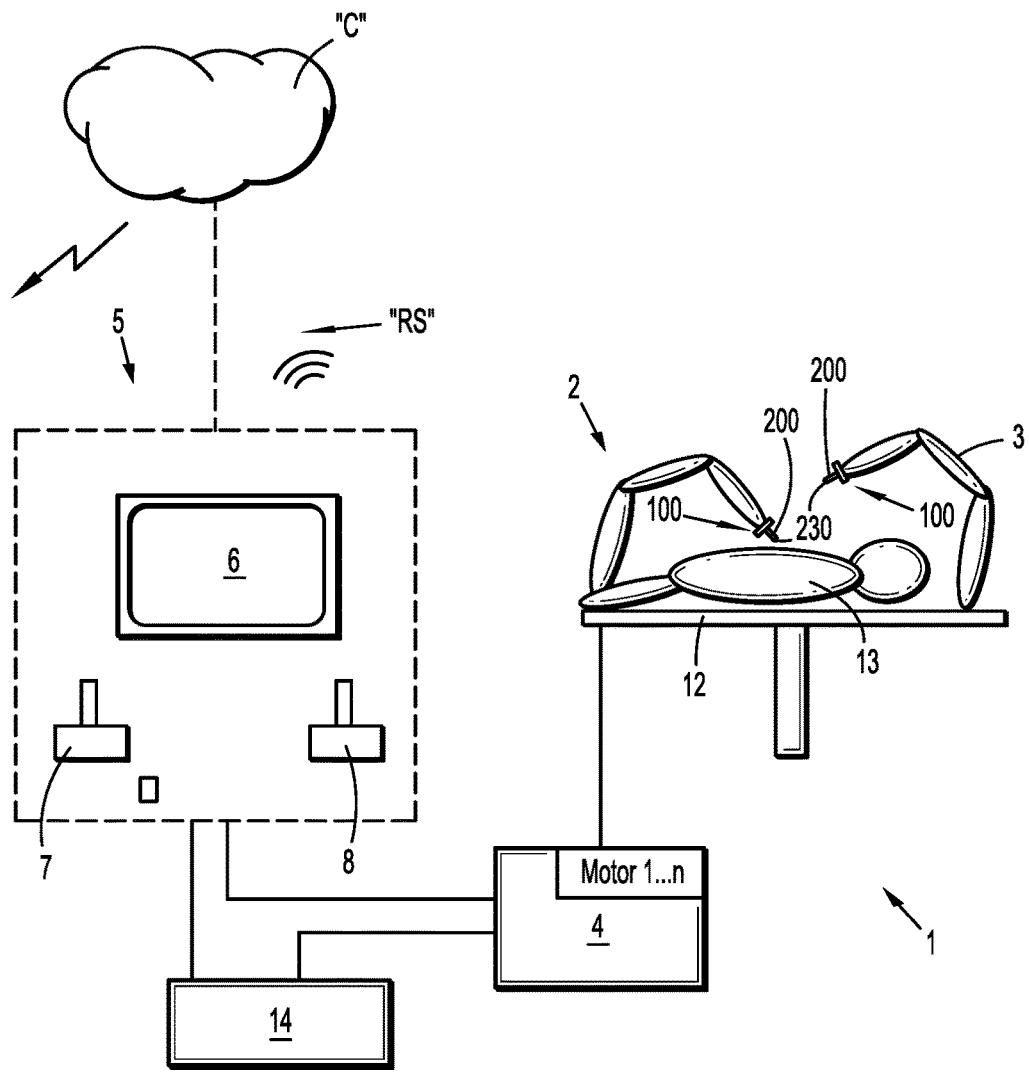
FIG. 1 is a schematic illustration of a surgical system in accordance with the present disclosure.

Embodiments of the present disclosure are described in detail with reference to the drawings, in which like reference numerals designate identical or corresponding elements in each of the several views. As used herein, the term "distal" refers to that portion of a device that is farther from the user, while the term "proximal" refers to that portion of a device that is closer to the user.

Referring initially to FIG. 1, a surgical system, such as, for example, a robotic surgical system is shown generally as surgical system 1 and generally includes a plurality of robotic arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 is composed of a plurality of members, which are connected through joints. System 1 also includes a surgical assembly 100 connected to a distal end of each of robotic arms 2, 3. A surgical instrument 200 supporting an end effector 230 may be attached to surgical assembly 100, in accordance with any one of several embodiments disclosed herein, as will be described in greater detail below.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their surgical assemblies 100 and/or surgical instruments 200 execute a desired movement according to a movement defined by means of manual input devices 7, 8. Control device 4 may also be set up in such a way that it regulates movement of robotic arms 2, 3 and/or of the drives.

Surgical system 1 is configured for use on a patient 13 lying on a patient table 12 to be treated in a minimally invasive manner by means of an end effector. Surgical system 1 may also include more than two robotic arms 2, 3, the additional robotic arms likewise being connected to control device 4 and being telemanipulatable by means of operating console 5. One or more additional surgical assemblies 100 and/or surgical instruments 200 may also be attached to the additional robotic arm.

Control device 4 may control a plurality of motors (Motor 1 . . . n) with each motor configured to drive a pushing or a pulling of one or more cables such as cables 216 (see FIG. 12) coupled to end effector 230 of surgical instrument 200. In use, as these cables are pushed and/or pulled, the one or more cables effect operation and/or movement of end effector 230 of surgical instrument 200. It is contemplated that control device 4 coordinates the activation of the various motors (Motor 1 . . . n) to coordinate a pushing or a pulling motion of one or more cables 216 in order to coordinate an operation and/or movement of one or more end effectors 230. In embodiments, each motor can be configured to actuate a drive rod or a lever arm to effect operation and/or movement of end effectors 230 in addition to, or instead of one or more cables.

Control device 4 can include any suitable logic control circuit adapted to perform calculations and/or operate according to a set of instructions. Control device 4 can be configured to communicate with a remote system "RS," either via a wireless (e.g., Wi-Fi, Bluetooth, LTE, etc.) and/or wired connection. Remote system "RS" can include data, instructions and/or information related to the various components, algorithms, and/or operations of work station 1. Remote system "RS" can include any suitable electronic service, database, platform, cloud "C" (see FIG. 1), or the like. Control device 4 may include a central processing unit operably connected to memory. The memory may include transitory type memory (e.g., RAM) and/or non-transitory type memory (e.g., flash media, disk media, etc.). In some embodiments, the memory is part of, and/or operably coupled to, remote system "RS."

Control device 4 can include a plurality of inputs and outputs for interfacing with the components of work station 1, such as through a driver circuit. Control device 4 can be configured to receive input signals and/or generate output signals to control one or more of the various components (e.g., one or more motors) of work station 1. The output signals can include, and/or can be based upon, algorithmic instructions which may be pre-programmed and/or input by a user. Control device 4 can be configured to accept a plurality of user inputs from a user interface (e.g., switches, buttons, touch screen, etc. of operating console 5) which may be coupled to remote system "RS."

A database 14 can be directly and/or indirectly coupled to control device 4. Database 14 can be configured to store pre-operative data from living being(s) and/or anatomical atlas(es). Database 14 can include memory which can be part of, and/or or operatively coupled to, remote system "RS."

Reference may be made to U.S. Patent Publication No. 2012/0116416, filed on Nov. 3, 2011, entitled "Medical Workstation," the entire content of which is incorporated herein by reference, for a detailed discussion of the construction and operation of surgical system 1.

Figure 2:
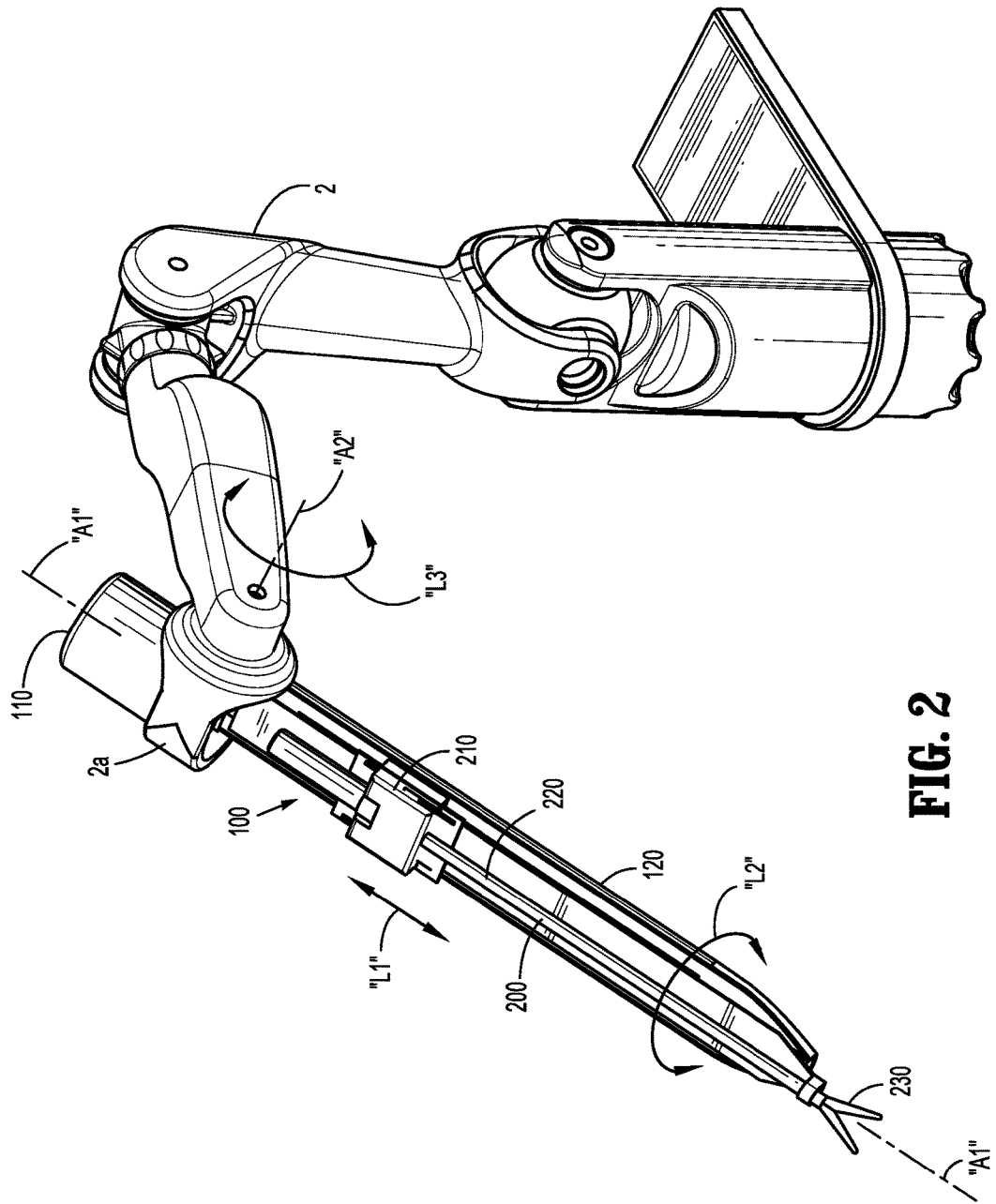
FIG. 2 is a perspective view of a surgical assembly of the surgical system of FIG. 1.
Figure 3:
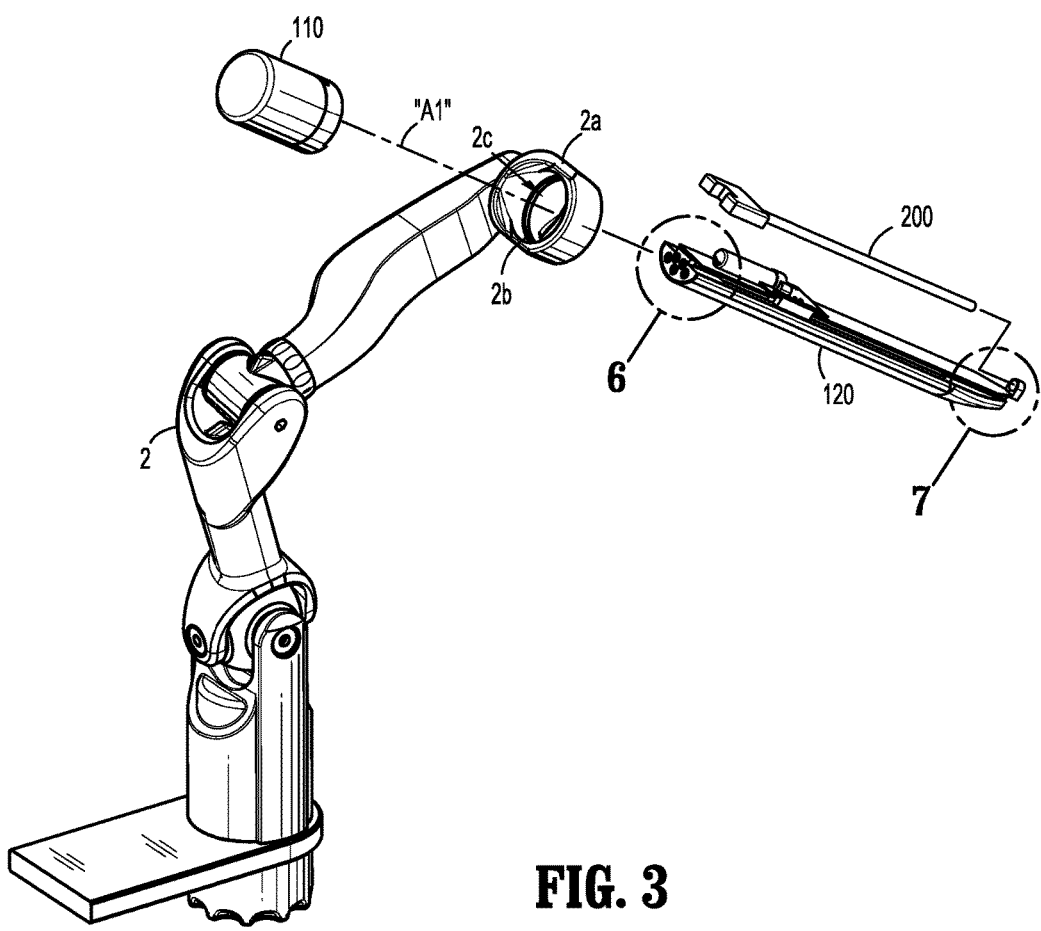
FIG. 3 is a perspective view, with parts separated, of the surgical assembly of FIG. 2.

Turning now to FIGS. 2 and 3, surgical assembly 100 includes an instrument drive unit 110 and an instrument support platform 120 releasably coupled to instrument drive unit 110. Surgical instrument 200 is releasably coupled to instrument support platform 120. As described in greater detail below, surgical instrument 200 is axially/longitudinally movable relative to instrument support platform 120, as illustrated by arrow "L1," and/or rotatable relative to a robotic arm such as robotic arm 2 as illustrated by arrows "L2" and "L3" (and/or rotatable relative to each of a pair of transverse axes "A1," "A2" extending through surgical assembly 100).

As described above, robotic arm 2 supports instrument support platform 120 and instrument drive unit 110. An arm mount 2a supported on a distal end of robotic arm 2 can include a ring gear 2b that engages with instrument drive unit 110. Ring gear 2b is fixed to arm mount 2a. In some embodiments, ring gear 2b is operatively coupled to a motor (not shown) that rotates ring gear 2b relative to arm mount 2a for imparting rotational movement to instrument drive unit 110, or portions thereof, about axis "A1" defined by arm mount 2a that extends centrally through an opening 2c defined by arm mount 2a, and which extends through instrument support platform 120.

Figure 4A:
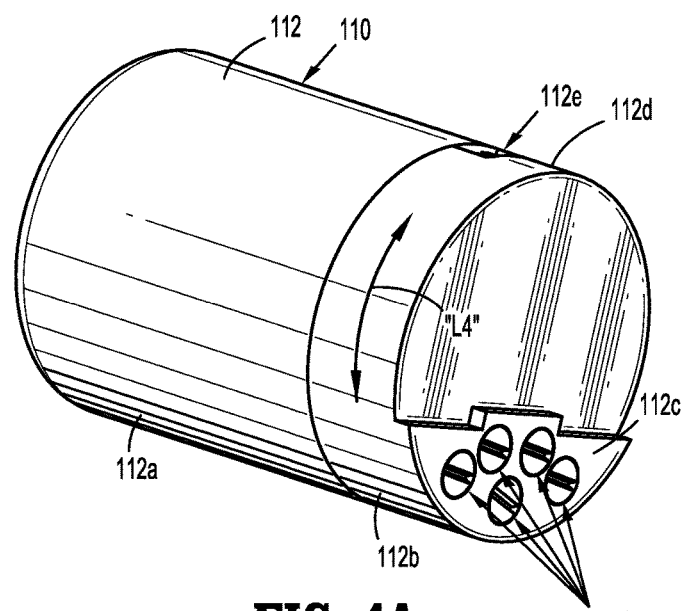
FIG. 4A is a front perspective view of an instrument drive unit of the surgical assembly shown in FIGS. 2 and 3.

With reference to FIG. 4A, instrument drive unit 110 includes a body 112 having a first housing portion 112a and a second housing portion 112b that extends distally from first housing portion 112a and is rotatably coupled thereto to enable second housing portion 112b to rotate relative to first housing portion 112a as illustrated by arrow "L4." In embodiments, first and second housing portion 112a, 112b are fixedly secured to one another such that first and second housing portions 112a, 112b are arranged to rotate together. Second housing portion 112b includes a connection surface 112c that extends distally therefrom to an end face. Connection surface 112c is engagable with a proximal end of instrument support platform 120. Second housing portion 112b includes a sidewall 112d that defines a gear aperture 112e therethrough. Connection surface 112c defines a plurality of drive member apertures 112f therethrough.

Figure 4B:
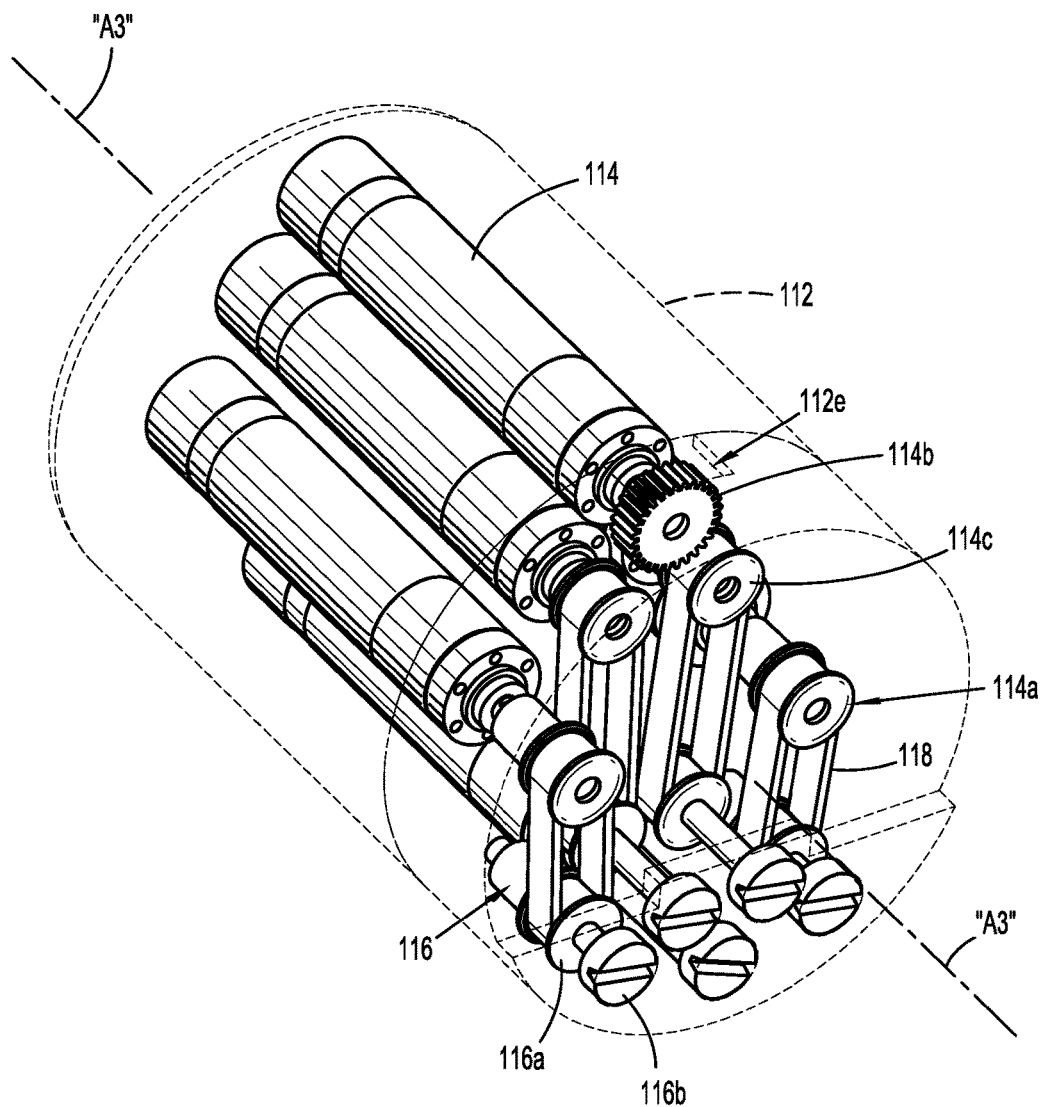
FIG. 4B is an enlarged perspective view with the body of the instrument drive unit of FIG. 4A shown in phantom.
Figure 7:
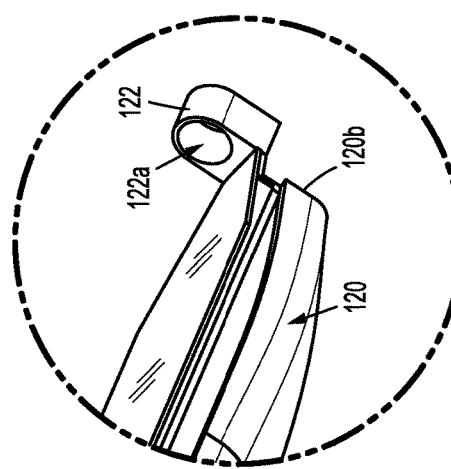
FIG. 7 is an enlarged perspective view of the indicated area of detail illustrated in FIG. 3.

As seen in FIG. 4B, body 112 supports a plurality of actuators or motors 114 and a plurality of transmission shafts 116. Each of the plurality of motors 114 includes a head 114a that extends distally from a respective motor 114 and that is rotatable relative to the respective motor 114. Each head 114a includes a drive gear 114b and/or a drive pulley 114c. One or more of these heads 114a can extend to from motors 114 in any suitable arrangement. For example, one or more heads 114a can be longitudinally aligned and/or offset relative to one another with respect to a longitudinal axis "A3" defined through instrument drive unit 110. Teeth of drive gear 114b are disposed in gear aperture 112e for enmeshing with teeth of ring gear 2b (FIG. 3) of arm mount 2a. Drive gear 114b can be any suitable gear such as a spur gear. Each transmission shaft 116 includes a driven pulley 116a and a drive head 116b supported on a distal end of a respective transmission shaft 116. One or more of drive pulleys 116a can be longitudinally aligned and/or offset relative to one another with respect to longitudinal axis "A3" so that drive pulleys 116a of transmission shafts 116 align with corresponding drive pulleys 114c of heads 114a. Body 112 further supports a plurality of drive belts 118. Each drive belt 118 couples one of the plurality of drive pulleys 114c of heads 114a to one of the plurality of driven pulleys 116a of transmission shafts 116 to impart a rotational force from a respective motor 114 to a corresponding transmission shaft 116.

Turning now to FIGS. 5-11, instrument support platform 120 extends longitudinally between a proximal end 120a and a distal end 120b and defines a pair of channels 120c, 120d (see FIG. 8) therein. The channels 120c, 120d are spaced-apart and extend longitudinally along instrument support platform 120. Proximal end 120a couples to connection surface 112c of instrument drive unit 110 and distal end 120b supports an instrument mount 122 that defines an instrument aperture 122a therethrough for receiving a shaft 220 (FIG. 12) of surgical instrument 200 therethrough.

Instrument support platform 120 supports a plurality of rotatable members 130 (e.g., transmission shafts), a sterile barrier 140 that covers the pair of channels 120c, 120d, and an instrument carriage 150. The plurality of rotatable members 130 is operably coupled to instrument carriage 150 and includes a first rotatable member 132, a pair of lower rotatable members 134a, 134b, and a pair of upper rotatable members 136a, 136b. In some embodiments, one or more of the plurality of rotatable members may be threadably engaged with instrument carriage 150, or portions thereof.

Each rotatable member 130 includes a driven proximal end 130a that is keyed to engage a respective drive head 116b of one of the plurality of transmission shafts 116 of instrument drive unit 110.

Figure 8:
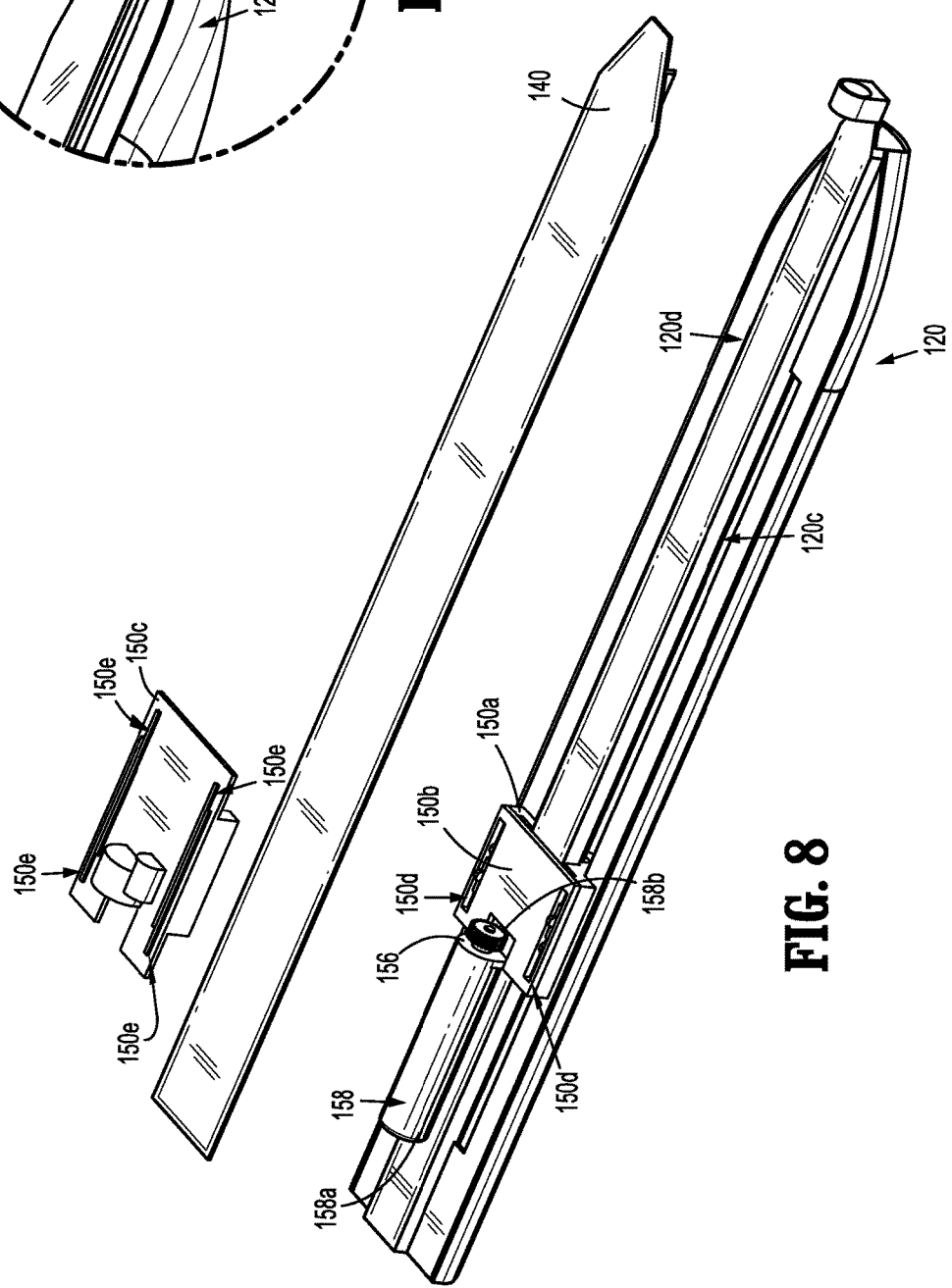
FIG. 8 is a side perspective view, with parts separated, of the instrument support platform shown in FIG. 5.

Instrument carriage 150 is supported in the pair of channels 120c, 120d of instrument support platform 120 and includes a carriage body 150a, a carriage lid 150b supported on carriage body 150a, and a carriage cover 150c positioned to cover carriage body 150a and carriage lid 150b (see FIG. 8). Carriage body 150a is threadably coupled to one of the plurality of rotatable members 130 for linear translation of instrument carriage 150 therealong as illustrated by arrow "L5" (see FIG. 11). Instrument carriage 150 further includes a plurality of linear drive members 152, each of which is threadably coupled to one of the plurality of rotatable drive members 130 for linear translation therealong. Carriage body 150a and each of the plurality of linear drive members 152 include a stepped configuration. The plurality of linear drive members 152 includes a pair of upper linear drive members 152a and a pair of lower linear drive members 152b that are each movable relative to one another and/or carriage body 150a in response to rotation of a respective one or more of the plurality of rotatable drive members 130 as illustrated by arrow "L6" (see FIG. 11). It is contemplated that one or more components of instrument carriage 150 can be independently movable relative to other components of instrument carriage 150. For instance, carriage body 150a and/or one or more of the plurality of drive members 152 can be independently movable relative to one another and/or simultaneously movable with one another.

Each of the plurality of linear drive members 152 supports an engagement rail 154 with a driving nub 154a. Each driving nub 154a projects through one of a plurality of slots 150d defined in lid 150b and one of a plurality of slots 150e defined through carriage cover 150c (see FIG. 8).

A rotary drive member 158 supported on carriage body 150a by a motor mount 156 includes a motor 158a having a rotary drive gear 158b coupled thereto. Teeth of rotary drive gear 158b enmesh with teeth of a secondary rotary drive gear 158c (see FIGS. 8 and 11).

With reference to FIG. 12, surgical instrument 200 defines a longitudinal axis "A4" and includes a housing 210 and a shaft 220 extending distally from housing 210. Housing 210 defines a plurality of slots 210a and supports a driven gear 212a that is secured to a distally extending rod 212b. Housing 210 further supports a plurality of linear driven members 214 including a first pair of linear driven members 214a and a second pair of linear driven members 214b. Each of the first and second pairs of linear driven members 214a, 214b is supported within the plurality of slots 210a and couples to one of driving nubs 154a of the plurality of linear drive members 152. Teeth of driven gear 212a enmesh with teeth of secondary drive gear 158c of instrument carriage 150 for imparting a rotational force to rod 212b within shaft 220. Rod 212b can couple to a transmission shaft (not shown) supported in end effector 230 to impart rotational forces to end effector 230, for example, to fire surgical staples (not shown) supported in end effector 230. For instance, U.S. patent application Ser. No. 14/257,063, filed Apr. 21, 2014, and entitled "Adapter Assembly with Gimbal for Interconnecting Electromechanical Surgical devices and Surgical Loading Units, and Surgical Systems Thereof," the entire contents of which are hereby incorporated by reference, describes surgical stapling devices with end effectors that support distally advanceable sleds operatively coupled to a rotatable transmission shaft to fire surgical staples. Each of a plurality of cables 216 have a first end that couples to one of the first and second pairs of linear driven members 214a, 214b and a second end that couples to end effector 230 at a distal end of shaft 220. Shaft 220 is dimensioned to receive each of the plurality of cables 216 and to enable each of the plurality of cables 216 to linearly translate therethrough. It is contemplated that cables 216 can operatively couple to end effector, for example, similar to the gimbal assembly described in U.S. patent application Ser. No. 14/257,063, filed Apr. 21, 2014, incorporated by reference hereinabove.

Figure 13:
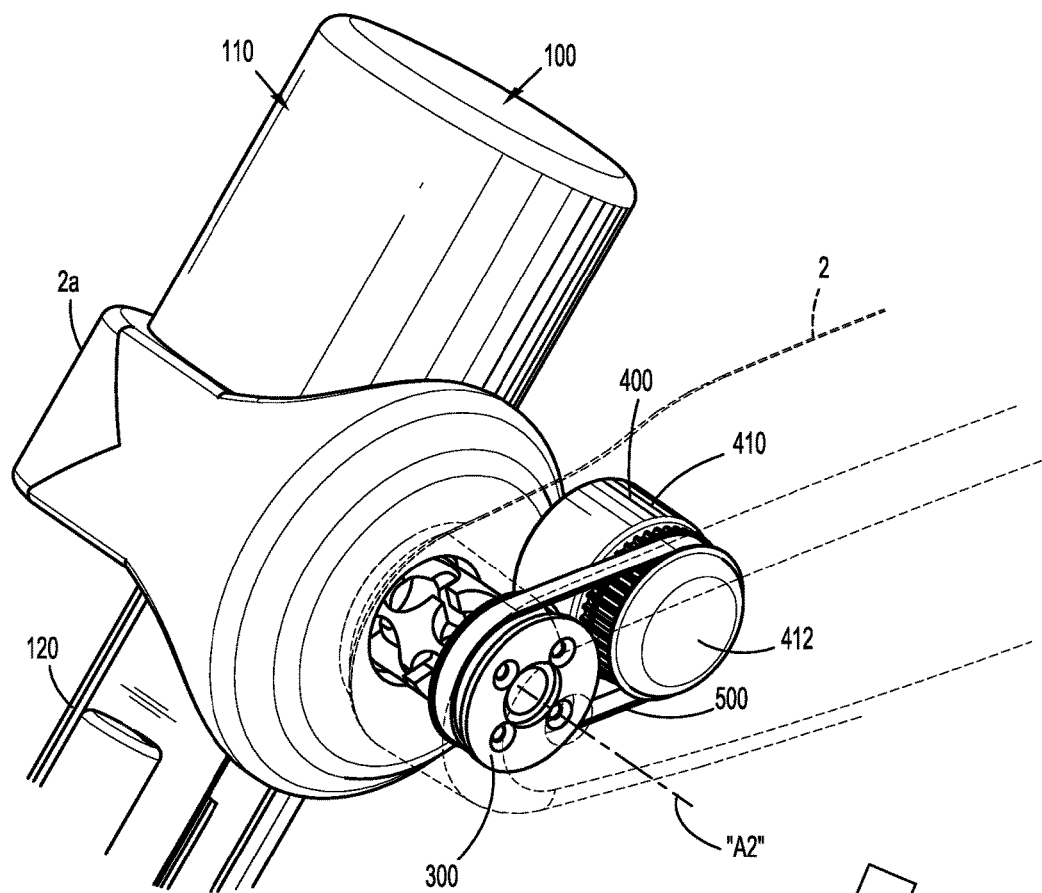
FIG. 13 is an enlarged perspective view of a portion of the surgical assembly shown in FIGS. 2 and 3 with a robotic arm connected thereto shown in phantom.
Figure 14:
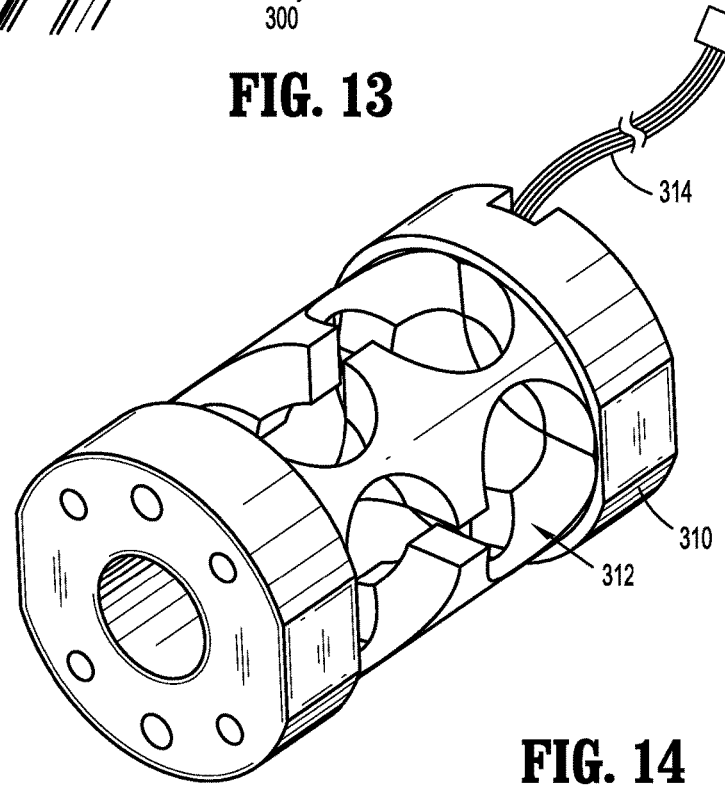
FIG. 14 is an enlarged perspective view of a torque sensor of the surgical assembly shown in FIG. 13.

As seen in FIG. 13, robotic arm 2 supports a rotatable torque sensor 300 and a motor assembly 400 that are coupled together by a drive belt 500. Torque sensor 300 is coupled to arm mount 2a and includes body 310 defining a plurality of exposed gauges 312. Body 310 supports electrical components (e.g., resistors, wires, etc.) 314 configured to communicate with control device 4 to provide torque feedback data, for example. Motor assembly 400 includes a motor 410 and a harmonic gear box 412 that cooperate to impart rotation on torque sensor 300 via drive belt 500 to effectuate rotation of arm mount 2a about axis "A2."

In operation, instrument drive unit 110 and instrument support platform 120 are coupled together and secured to arm mount 2a such that the plurality of transmission shafts 116 are engaged with the plurality of rotatable members 130. With surgical instrument 200 removably coupled to instrument support platform 120, one or more of the plurality of motors 114 are activated to rotate one or more of the plurality of transmission shafts 116.

Rotation of drive gear 114b rotates second housing portion 112b of instrument drive unit 110 relative to first housing portion 112a. As second housing portion 112b rotates within arm mount 2a and along gear 2b of arm mount 2a, instrument support platform 120 rotates with second housing portion 112b (simultaneously) to effectuate rotation of surgical instrument 200 about axis "A1" defined by arm mount 2a. Surgical instrument 200 can be positioned on instrument support platform 120 so that axis "A4" of surgical instrument 200 is axially aligned with axis "A1" of arm mount 2a to enable coaxial rotation of surgical instrument 200 about axis "A1" as instrument drive unit 110, or portions thereof, rotate about axis "A1." In some embodiments, surgical instrument 200 can be positioned on instrument support platform 120 so that axis "A4" of surgical instrument 200 is axially offset from (e.g., parallel to) axis "A1" of arm mount 2a to enable orbital rotation of surgical instrument 200 about axis "A1."

Rotation of each transmission shaft 116 rotates one of the plurality of rotatable members 130 to longitudinally translate instrument carriage 150 and/or one or more of the plurality of linear drive members 152. Rotation of first rotatable member 132 longitudinally translates instrument carriage 150 through the pair of channels 120c, 120d of instrument support platform 120. Longitudinal movement of instrument carriage 150 relative to instrument support platform 120 longitudinally translates surgical instrument 200 relative to instrument support platform 120. Rotation of one or both of the pair of lower rotatable members 134a, 134b and/or one or both of the pair of upper rotatable members 136a, 136b longitudinally translates respective ones of the plurality of linear drive members 152 relative to instrument carriage 150 and/or one or more of the other ones of the plurality of linear drive members 152.

With the plurality of linear drive members 152 of instrument carriage 150 engaged with the plurality of linear driven members 214 of surgical instrument 200 via driving nubs 154a, longitudinal movement of one or more of the plurality of linear drive members 152 longitudinally moves one or more of the plurality of linear driven members 214 to longitudinally move one or more of the plurality of cables 216.

An activation of motor 158a of rotary drive member 158 rotates rotary drive gear 158 to rotate secondary rotary drive gear 158c. Rotation of secondary rotary drive gear 158c rotates driven gear 212a of surgical instrument 200 to rotate rod 212b of surgical instrument 200.

Rotation of rod 212b and/or longitudinal translation of one or more of the plurality of cables 216 imparts movement (e.g., rotation, pivoting, articulation, longitudinal/lateral translation, etc.) on end effector 230, or portions thereof, relative to instrument support platform 120 and/or effectuates a firing of end effector 230.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical system for selective connection to a robotic arm, the surgical system comprising:
   an instrument drive unit including a plurality of actuators;
   an instrument support platform configured to be releasably coupled to the instrument drive unit in an arm mount of the robotic arm, the arm mount defining a central longitudinal axis and including a ring gear that encircles the central longitudinal axis of the arm mount, the ring gear configured to engage the instrument drive unit to rotate the instrument drive unit relative to the arm mount about the central longitudinal axis of the arm mount, the instrument support platform including a plurality of rotatable members operably associated with the plurality of actuators of the instrument drive unit, each of the plurality of rotatable members being rotatable in response to actuation of at least one of the plurality of actuators;
   an instrument carriage coupled to the plurality of rotatable members of the instrument support platform and including a plurality of drive members, at least one of the plurality of drive members being translatable in response to rotation of at least one of the plurality of rotatable members; and
   a surgical instrument releasably coupled to the instrument carriage and supporting an end effector that extends distally from the instrument support platform, the end effector being movable in response to translation of at least one of the plurality of drive members of the instrument carriage.

2. The surgical system of claim 1, wherein at least one of the plurality of drive members rotates a first driven member of the surgical instrument and at least one of the plurality of drive members linearly translates a second driven member of the surgical instrument, wherein in response to movement of a respective one of the first and second driven members, the respective one of the first and second driven members is configured to effectuate at least one of: 1) movement of the end effector relative to the instrument support platform or 2) firing of the end effector.

3. The surgical system of claim 2, wherein at least one of the plurality of drive members includes a drive gear that is configured to engage a driven gear of the first driven member.

4. The surgical system of claim 2, wherein at least one of the first and second driven members includes a cable that operatively couples to the end effector.

5. The surgical system of claim 2, wherein at least one of the first and second driven members includes a rod that operatively couples to the end effector.

6. The surgical system of claim 1, wherein rotation of at least one of the plurality of rotatable members linearly translates a carriage body of the instrument carriage through at least one channel defined by the instrument support platform to move the instrument carriage relative to the instrument support platform.

7. The surgical system of claim 6, wherein a barrier covers the at least one channel.

8. The surgical system of claim 7, wherein the at least one channel includes a plurality of spaced apart channels that extend longitudinally along the instrument support platform.

9. The surgical system of claim 1, wherein the instrument drive unit includes a gear actuatable by one of the plurality of actuators, the instrument support platform and the surgical instrument being simultaneously rotatable about a longitudinal axis defined through the instrument support platform in response to actuation of the gear.

10. The surgical system of claim 1, wherein the plurality of actuators of the instrument drive unit is controlled by telemanipulation.

11. A robotic surgical assembly, comprising:
    a robotic arm including an arm mount having an annular configuration, the arm mount defining a central longitudinal axis and including a ring gear that encircles the central longitudinal axis of the arm mount;
    an instrument drive unit secured to the arm mount and including a plurality of actuators, the ring gear configured to engage the instrument drive unit to rotate the instrument drive unit relative to the arm mount about the central longitudinal axis of the arm mount;
    an instrument support platform defining a longitudinal axis and releasably coupled to the instrument drive unit in the arm mount, the instrument support platform including a plurality of rotatable members operably associated with the plurality of actuators of the instrument drive unit, each of the plurality of rotatable members being rotatable in response to an actuation of at least one of the plurality of actuators of the instrument drive unit; and
    an instrument carriage coupled to the plurality of rotatable members and including at least one rotary drive member that rotates about the longitudinal axis of the instrument support platform and at least one linear drive member that linearly translates along the longitudinal axis of the instrument support platform, at least one of the linear or rotary drive members being movable in response to rotation of at least one of the plurality of rotatable members of the instrument support platform.

12. The robotic surgical assembly of claim 11, wherein rotation of at least one of the plurality of rotatable members linearly translates a carriage body of the instrument carriage through at least one channel defined by the instrument support platform to move the instrument carriage relative to the instrument support platform.

13. The robotic surgical assembly of claim 12, wherein a barrier covers the at least one channel.

14. The robotic surgical assembly of claim 11, wherein the at least one channel includes a plurality of spaced apart channels that extend longitudinally along the instrument support platform.

15. The robotic surgical assembly of claim 11, wherein the plurality of actuators of the instrument drive unit is controlled by telemanipulation.

16. The robotic surgical assembly of claim 11, wherein the instrument drive unit and the arm mount include gears that engage one another to enable an end face of the instrument drive unit to rotate about a longitudinal axis defined through the instrument drive unit, wherein the instrument support platform is connectable to the end face of the instrument drive unit so that that rotation of the end face imparts rotation on the instrument support platform.

17. The robotic surgical assembly of claim 11, wherein the arm mount is coupled to the robotic arm and positioned to rotate relative to the arm mount about an axis that extends transverse to the central longitudinal axis of the arm mount.

18. A surgical assembly for supporting a surgical instrument having an end effector, the surgical assembly comprising:
an instrument drive unit;
an instrument support platform defining a longitudinal axis and configured to releasably couple to the instrument drive unit in an arm mount of a robotic arm, the instrument support platform including a plurality of rotatable members, the arm mount defining a central longitudinal axis and including a ring gear that encircles the central longitudinal axis of the arm mount, the ring gear configured to engage the instrument drive unit to rotate the instrument drive unit relative to the arm mount about the central longitudinal axis of the arm mount;
an instrument carriage coupled to the plurality of rotatable members and including at a rotary drive member that rotates about the longitudinal axis of the instrument support platform and a plurality of linear drive members that linearly translates along the longitudinal axis of the instrument support platform, the rotary drive member configured to fire the end effector in response to rotation of a first one of the plurality of rotatable members of the instrument support platform, at least one of the plurality of linear drive members configured to move the end effector relative to the support platform in response to rotation of a second one of the plurality of rotatable members of the instrument support platform.

19. The surgical assembly of claim 18, wherein a third one of the plurality of rotatable members of the instrument support platform linearly translates a carriage body of the instrument carriage through at least one channel defined by the instrument support platform to move the instrument carriage relative to the instrument support platform.

20. The surgical assembly of claim 18, wherein a first one of the plurality of rotatable members rotates independent of the second one of the plurality of rotatable members.

21. The surgical assembly of claim 18, wherein the instrument drive unit includes a plurality of actuators that are controlled by telemanipulation.

* * * * *